United States Patent [19]

Stobie

[11] Patent Number: 4,815,471

[45] Date of Patent: Mar. 28, 1989

[54] CATHETER ASSEMBLY

[75] Inventor: John J. Stobie, Portland, Oreg.

[73] Assignee: Precision Interconnect Corporation, Portland, Oreg.

[21] Appl. No.: 226,857

[22] Filed: Aug. 1, 1988

[51] Int. Cl.⁴ ............................................. A61B 5/02
[52] U.S. Cl. .................................. 128/675; 128/635; 128/748; 73/716
[58] Field of Search ............................... 128/672–675, 128/748, 632, 635, 637, 670; 73/706, 716, 720–721, 756

[56] References Cited

U.S. PATENT DOCUMENTS

| | | | |
|---|---|---|---|
| 4,023,562 | 5/1977 | Hynecek et al. | 128/748 |
| 4,201,222 | 5/1980 | Haase | 128/673 X |
| 4,274,423 | 6/1981 | Mizune et al. | 128/675 |
| 4,456,013 | 6/1984 | De Rossi et al. | 128/675 |
| 4,534,355 | 8/1985 | Potter | 128/635 |
| 4,554,927 | 11/1985 | Fussell | 128/670 |
| 4,683,757 | 8/1987 | Adams et al. | 73/756 |
| 4,685,469 | 8/1987 | Keller | 128/748 X |
| 4,722,348 | 2/1988 | Ligtenberg et al. | 128/675 |
| 4,727,730 | 3/1988 | Boiarski et al. | 128/667 |
| 4,730,622 | 3/1988 | Cohen | 128/748 X |

FOREIGN PATENT DOCUMENTS 2108675  5/1983  United Kingdom .............. 128/748

Primary Examiner—Kyle L. Howell
Assistant Examiner—Angela D. Sykes
Attorney, Agent, or Firm—Chernoff, Vilhauer, McClung & Stenzel

[57] ABSTRACT

A compact catheter assembly provides for the communication of a reference pressure to a pressure-sensing transducer by forming a passageway between spaced electrical conductors mounted on a planar dielectric substrate. The cathter assembly also provides for the operative mounting of multiple transducers onto a single catheter tip by employing a plurality of planar dielectric substrates, each having an array of electrical conductors, stacked atop one another so as to protrude longitudinally from the end of the catheter bore at different distances. A plurality of electrical transducers protrude longitudinally in series from the bore overlying the substrates.

10 Claims, 1 Drawing Sheet

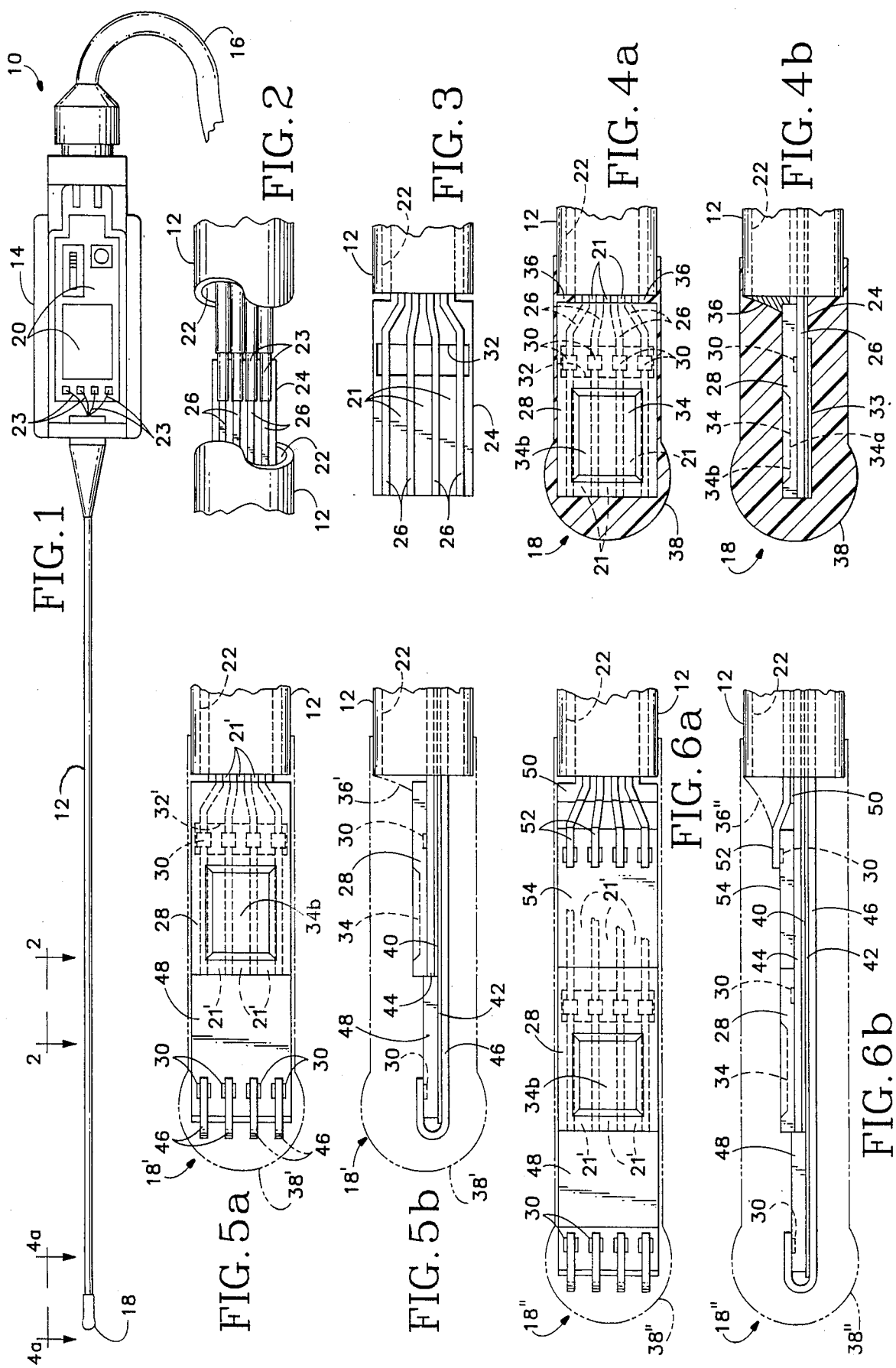

CATHETER ASSEMBLY

BACKGROUND OF THE INVENTION

The present invention relates to a catheter assembly insertable into a living body for biophysical (e.g. blood pressure or flow rate) or biochemical (e.g. blood pH or oxygen concentration) sensing at a region of interest. More particularly, the invention relates to compact configurations for such a catheter assembly adapting it for insertion through or into exceptionally small spaces, and for measuring multiple parameters simultaneously without sacrificing compactness.

Many prior art catheter assemblies, such as those shown in Mizuno et al., U.S. Pat. Nos. 4,274,423, DeRossi et al., 4,456,013, Adams et al., 4,683,757 and Ligtenberg et al., 4,722,348, employ solid-state electronic pressure transducers at their insertable ends. Such transducers have a pressure-sensing diaphragm, one side of which is exposed to the pressure to be measured and the other side of which communicates with a reference pressure passageway which extends into the catheter tube and is isolated from the pressure to be measured. To provide the reference pressure passageway, a special mounting structure for the pressure transducer must be included at the insertable end of the catheter assembly, increasing the transverse cross-sectional diameter of the insertable end and limiting the functions which it can perform within the available space.

Other types of transducers which are conventionally employed in catheter assemblies are those categorized generally as chemically sensitive semiconductor devices, or CHEMFETS. These solid-state electronic chemical transducers are capable of performing chemical analysis of blood and other fluids by ion detection, and measuring pH, gases, humidity, enzymes and other parameters. Despite the variety of available transducers, however, catheters usually employ only a single solid-state device at their insertable ends for measuring a single parameter, such as pressure. Such single-function devices require the sequential removal and insertion of multiple catheters having different transducers to obtain substantially contemporaneous readings of multiple parameters at a region of interest, but such multiple insertions increase the risk of injury to the patient as well as the time and expense of the procedure. Also, multiple insertions cannot simultaneously measure multiple parameters at an identical site to correlate exactly the relationship between the parameters. Although multi-function cathether assemblies having multiple transducers at their insertable ends have also been used in the past, such catheter assemblies have been limited with respect to their number of multiple functions primarily by space limitations affecting the maximum permissible transverse cross-sectional dimension of their insertable tips, dictated by the small areas of the blood vessels or other passageways into which the tips must be inserted.

Therefore, a need exists for catheter assemblies having an insertable tip of minimized transverse cross-section, yet capable of measuring pressure and simultaneously measuring multiple parameters.

SUMMARY OF THE INVENTION

A first aspect of the present invention eliminates the need for a special mounting structure for a pressure transducer having a reference pressure passageway. Instead, a plurality of spaced electrical conductors mounted longitudinally on a planar dielectric substrate for connection to the transducer protrude from the catheter bore so as to define a longitudinal passageway between the conductors. The pressure-sensing diaphragm of the solid-state pressure transducer overlies the conductors so that one side of the diaphragm is in communication with the passageway which extends into the catheter bore. The assembly is sealed so as to isolate the passageway from the opposite side of the diaphragm.

The present invention also provides for the assembly of multiple transducers in a single catheter tip by stacking a plurality of elongated, planar dielectric substrates in parallel relation atop one another so as to protrude from the end of the catheter bore at different distances. A plurality of electrical transducers overlie the dielectric substrates so as to protrude longitudinally in series from the end of the catheter bore. Each transducer is operatively coupled to a different array of electrical conductors mounted longitudinally on the respective dielectric substrates.

Accordingly, it is a principal object of the present invention to provide a compact catheter assembly having a pressure sensor mounting structure at its insertable tip in which the reference pressure connection is formed by the channels between the spaced electrical conductors on a dielectric substrate.

It is a further object of the present invention to provide a catheter assembly having an insertable tip structure of minimized transverse cross-section which nevertheless mounts multiple solid-state transducers for simultaneous measurement of a combination of parameters.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a side elevational view of an exemplary embodiment of a catheter assembly of the present invention.

FIG. 2 is an enlarged plan view, partially cut away, taken along line 2—2 of FIG. 1 illustrating the interconnection between the substrate-mounted conductors and electrical cables within the catheter bore.

FIG. 3 is an enlarged plan view of the dielectric substrate and associated conductor array as it emerges from the insertable end of the catheter of FIG. 1.

FIG. 4a is an enlarged partially sectional plan view taken along line 4a—4a of FIG. 1 showing an embodiment of a single-transducer catheter tip according to the present invention.

FIG. 4b is an enlarged partially sectional side view of the catheter tip of FIG. 4a.

FIG. 5a is an enlarged plan view showing an embodiment of a dual-transducer catheter tip according to the present invention.

FIG. 5b is an enlarged side view of the catheter tip of FIG. 5a.

FIG. 6a is an enlarged plan view showing an embodiment of a three-transducer catheter tip according to the present invention.

FIG. 6b is an enlarged side view of the catheter tip of FIG. 6a.

DESCRIPTION OF THE PREFERRED EMBODIMENT

Referring to the drawings, and in particular to FIG. 1, a preferred embodiment of the present invention is shown as comprising a catheter assembly 10 having a catheter tube 12, circuitry module 14 and electrical connector cable 16. The catheter 12 is preferably composed of polyurethane material of the type disclosed, for example, in U.S. Pat. Nos. 4,447,590 and 4,523,005 which are incorporated herein by reference. The catheter includes a tip 18 at one end thereof for insertion into a living body, the tip containing one or more solid-state transducers, each for the direct measurement in vitro of a desired parameter at a region of interest. The transducers may be of any type requiring electrical connections, and normally will employ semiconductor material constructed for developing an electrical signal representative of the parameter to be monitored. The signal is conducted to detector circuitry 20 through an interior cathetor bore 22 extending axially through the length of the catheter 12.

In one embodiment of the present invention, illustrated in FIGS. 2, 3, 4a and 4b, the catheter assembly 10 employs a tip 18 having a single, elongate, planar dielectric substrate 24 which protrudes longitudinally outwardly from the bore 22 at the end of the catheter 12, as shown in FIG. 3. The substrate is preferably made of a flexible polyimide material and has a plurality of electrical conductors 26 configured longitudinally by standard photolithographic techniques in a transversely spaced array protruding perpendicularly to the plane of the substrate. Portions of the substrate 24 and conductors 26 preferably extend into the bore as far as an interconnection, shown in FIG. 2, between the substrate-mounted conductors 26 and coaxial cables 23 electrically joined to the detector circuitry 20. As shown in FIGS. 3 and 4a, the transverse spacing between the conductors 26 as they protrude outwardly from the end of the bore 22 is greater than the spacing of the conductors extending into the bore. A pressure sensing transducer 28 is operatively mounted atop the protruding portions of the conductors and substrate so as to overlie both. Each of a plurality of bond pads 30 on the transducer are thermosonically bonded to a respective conductor 26, access for such bonding being provided by an aperture 32 cut into the substrate 24. Normally the bond pads 30 are of aluminum or gold, aluminum being preferable for economy of manufacture, while the conductors 26 are of gold-plated copper. A polyimide plate 33 (FIG. 4b) is adhered to the bottom of the substrate to close the aperture 32 following bonding. The transducer 28 includes a presssure sensitive diaphragm 34 having an inner side 34a and an outer side 34b. The inner side 34a of the diaphragm is exposed to one or more passageways 21 defined between adjacent conductors 26, which serve as reference pressure passageways. Each of the passageways 21 is sealed from exposure to pressure on the outer side 34b of the diaphragm by the plate 33 and by an epoxy or other high-viscosity sealant layer 36 (FIG. 4b) at the end of the bore 22 where the substrate and conductors emerge therefrom. The tip is preferably completed by applying a pliable layer of polyurethane 38, which may be of the type employed in the catheter tube, onto the perimeter of tip 18, such layer being sufficiently flexible to permit the outer side 34b of the diaphragm to sense external pressure. The polyurethane also seals the outer extremities of the passageways 21 from exposure to the sensed external pressure. Both the epoxy adhesive 36 and the polyurethane 38, when liquid, are sufficiently viscous to avoid wicking into the passageways 21 and obstructing them.

In an alternative embodiment of the present invention shown in FIGS. 5a and 5b, catheter tip 18' includes dual elongate, planar dielectric substrates 40, 42 stacked in parallel, back-to-back relation to each other, the substrates protruding longitudinally at different distances outwardly from the end of the bore 22. A respective array of electrical conductors 44, 46 is mounted longitudinally to each of the respective substrates 40, 42. A pressure sensing transducer 28 is mounted, as described previously, atop the conductors 44 overlying substrate 40 and having one side of its diaphragm 34 exposed to passageways 21' between the conductors. A solid-state chemical transducer 48 is positioned longitudinally in series to transducer 28, in end-to-end relation thereto and overlying substrate 42 so as to protrude longitudinally outwardly from the end of cathether 12 to a greater extent than transducer 28. Both transducers 28 and 48 overlap each other vertically, intersecting a common plane parallel to the substrates 40, 42 and thereby requiring no significant increase in the transverse cross-sectional diameter of the tip from that required for the single-function tip of FIGS. 4a and 4b. The transducer 28 is operatively coupled to the array of conductors 44 as previously described, with the exception that substrate 42 serves to close the aperture 32' in lieu of the plate 33, and transducer 48 closes the ends of passageways 21'. The transducer 48 is adhered by epoxy directly atop substrate 42 with bond pads 30 outwardly directed. The array of conductors 46 are coupled to the pads 30 of transducer 48 by extension of the conductors from beneath the transducer 48 beyond the outward extremity thereof, reversing direction so as to overlie the transducer 48.

In a third embodiment of the present invention shown in FIGS. 6a and 6b a catheter tip 18" includes three elongate, planar dielectric substrates 40, 42, 50 stacked in parallel relation to each other and protruding longitudinally at different distances outwardly from the end of bore 22. Substrates 40 and 42, their arrays of conductors 44 and 46, and their transducers 28 and 48 are arranged identically to FIGS. 5a and 5b. However, an additional solid-state chemical transducer 54 overlies the substrate 40 so as to be positioned longitudinally in series with the other two transducers. Transducer 54 has bond pads 30 connected to conductors 52 on substrate 50 which extend upwardly from substrate 50 to the pads. The transducers 28, 48, and 54 all overlap each other vertically so as to intersect a common plane parallel to substrates 40, 42, 50 and thereby require no significant increase in the transverse cross-sectional diameter of tip 18", as compared to tips 18 and 18', despite the fact that tip 18" is capable of performing three measurement functions simultaneously. Comparable stacking of additional substrates and serial positioning of additional transducers at different degrees of protrusion from the catheter bore can be employed to provide still greater numbers of functions while retaining the compact configuration of the tip.

The passageways 21' in FIGS. 5a, 5b, 6a and 6b are sealed from the outer side 34b of the diaphragm 34 as previously described with reference to FIGS. 4a and 4b by epoxy sealant 36' and 36", respectively. If a pliable layer 38' or 38" is employed over the chemical transducers 48 and 54, it should be sufficiently permeable to ions to avoid any interference with the operation of the chemical transducers.

The terms and expressions which have been employed in the foregoing abstract and specifiction are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A medical diagnostic device comprising:
 (a) an elongate catheter having an elongate interior bore and an end for insertion into a living body;
 (b) a planar dielectric substrate attached to said catheter so as to protrude longitudinally outwardly from said interior bore at said end;
 (c) a plurality of electrical conductors mounted longitudinally on said dielectric substrate in a transversely spaced array protruding from said substrate in a direction normal to the plane thereof so as to define a longitudinal passageway between adjacent conductors, said array having an exterior end protruding longitudinally outwardly from said bore;
 (d) a pressure-sensing transducer having a pressure-sensing diaphragm with respective inner and outer sides, said transducer being mounted on said array of conductors so as to protrude longitudinally outwardly from said bore with said inner side of said diaphragm in communication with said passageway; and
 (e) means connecting said passageway with said bore and isolating said passageway from said outer side of said diaphragm.

2. The device of claim 1 wherein a portion of said array extends into said bore, the transverse spacing between said conductors being greater in the portion of said array protruding longitudinally outwardly from said bore than in the portion of said array extending into said bore.

3. The device of claim 1, including a plurality of bond pads on said transducer attached operatively to said array of conductors.

4. The device of claim 3, further including means defining an aperture in said dielectric substrate for providing access for attaching said conductors to said bond pads.

5. A medical diagnostic device comprising:
 (a) an elongate catheter having an elongate interior bore and an end for insertion into a living body;
 (b) a plurality of planar dielectric substrates in parallel relation one above the other and protruding longitudinally at different distances outwardly from said end;
 (c) a plurality of arrays of electrical conductors, each array being mounted longitudinally on a respective one of said dielectric substrates; and
 (d) respective first and second electrical transducers protruding longitudinally in series outwardly from said end, each transducer overlying a dielectric substrate and being operatively coupled to a respective different array of said electrical conductors.

6. The device of claim 5 wherein said first electrical transducer overlies both of said dielectric substrates and said second electrical transducer overlies one, but not the other, of said dielectric substrates.

7. The device of claim 5 wherein said first and second electrical transducers both intersect a common plane parallel to said planar dielectric substrates.

8. The device of claim 5, further including a third electrical transducer overlying one of said dielectric substrates and protruding outwardly from said end longitudinally in series with said first and second transducers, said third transducer and at least one of said first and second transducers both intersecting a common plane parallel to said planar dielectric substrates.

9. The device of claim 5 wherein at least one of said transducers and at least one of said dielectric substrates both intersect a common plane parallel to said planar dielectric substrates.

10. The device of claim 5 wherein the array of electrical conductors mounted on at least one of said dielectric substrates is coupled to a respective transducer overlying the substrate by extending from beneath the respective transducer longitudinally outwardly beyond the outward extremity of the respective transducer and reversing direction so as to overlie the respective transducer.

* * * * *

UNITED STATES PATENT AND TRADEMARK OFFICE
CERTIFICATE OF CORRECTION

PATENT NO. : 4,815,471

DATED : March 28, 1989

INVENTOR(S) : John J. Stobie

It is certified that error appears in the above-identified patent and that said Letters Patent is hereby corrected as shown below:

On the title page,
in the Abstract:  Change "cathter" to --catheter--.

Col. 2, Line 9  Change "t" to --to--.

Signed and Sealed this

Eighteenth Day of September, 1990

Attest:

HARRY F. MANBECK, JR.

*Attesting Officer*  Commissioner of Patents and Trademarks